United States Patent [19]

Longley et al.

[11] 4,117,237
[45] Sep. 26, 1978

[54] UNSYMMETRICAL SULFOSUCCINATE DIESTERS

[75] Inventors: Kermit D. Longley, Park Forest; Anastasios J. Karalis, Chicago, both of Ill.

[73] Assignee: Witco Chemical Corporation, New York, N.Y.

[21] Appl. No.: 701,485

[22] Filed: Jun. 30, 1976

Related U.S. Application Data

[63] Continuation of Ser. No. 497,550, Aug. 14, 1974, abandoned.

[51] Int. Cl.² .............. C07C 143/12; C07C 143/14; C07D 295/22
[52] U.S. Cl. .................................. 560/151; 252/354; 252/545; 252/557; 260/29.6 R; 544/110
[58] Field of Search ............... 260/481 R; 252/557, 252/354, 545; 560/151; 544/110

[56] References Cited

U.S. PATENT DOCUMENTS

| 2,028,091 | 1/1936 | Jaeger | 260/481 R |
| 2,176,423 | 10/1939 | Jaeger | 260/481 R |
| 2,507,030 | 5/1950 | Lynch | 260/481 R |
| 3,640,882 | 2/1972 | Grooves, Jr. | 260/481 R |

Primary Examiner—Vivian Garner
Attorney, Agent, or Firm—Albert L. Gazzola; Morton Friedman

[57] ABSTRACT

Unsymmetrical sulfosuccinate diesters in which one carboxyl group of the sulfosuccinate is esterified with an alcohol, for instance, a $C_8$-$C_{12}$ aliphatic monohydric such as octyl or dodecyl alcohol, or with an ethoxylated or propoxylated alkyl phenol, and in which the other carboxyl group is esterified by reaction with an α-monoepoxide such as propylene oxide, or higher α-epoxides. The said diesters have utility as surfactants, such as detergents and emulsifiers.

8 Claims, No Drawings

UNSYMMETRICAL SULFOSUCCINATE DIESTERS

This is a continuation of Application Ser. No. 497,550, filed Aug. 14, 1974, now abandoned.

Our invention relates to the preparation of certain types of novel unsymmetrical sulfosuccinate diesters at least most of which can be represented by the following formula:

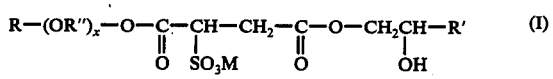

where:

R = $C_1$-$C_{20}$ alkyl, or alkylbenzene radical having at least 1 but not more than 3, nuclearly attached alkyl groups and at least 1, but not more than 2 of these alkyl groups containing 5 to 12 carbon atoms and the said such other alkyl group or groups as may be present, containing 1 to 3 carbon atoms.

R' = alkyl containing 1 to 18 carbon atoms or benzene radical

R" = ethylene or propylene.

x = 0 to 6 and is at least 1 when R = alkylbenzene radical.

with the proviso that the sum of the number of carbon atoms in R and R' is from 5 to 33 and that there is a difference in the number of carbon atoms in R and R' which difference is at least 4; and M is a cation selected from the group of alkali metals (including ammonium), alkaline earth metals, and organic substituted ammonium or amines. Most desirably, the difference in the number of carbon atoms between R and R' is from 6 to 16. Again, most desirably, in the novel compounds of our present invention, R is alkyl containing from 8 to 15 carbon atoms and R' is a methyl group. Others are those in which R is a $C_1$-$C_3$ alkyl radical and R' is an alkyl radical containing from 6 to 10 carbon atoms.

It is particularly desirable that the novel sulfosuccinate compounds of our present invention be marketed and used in the form of the aforementioned types of salts, that is, where M in formula (I) is an alkali metal (which term is here used to mean sodium, potassium, lithium, and ammonium), or alkaline earth metals; namely, calcium, magnesium, strontium, and barium; or, as noted above, organic substituted ammonium or amines. These latter, which most advantageously are water-soluble lower molecular weight amines, may be selected from a wide group, typical examples of which are dimethylamine, diethylamine, triethylamine, propylamine, monoisopropylamine, di-isopropylamine, tri-isopropylamine, and commercial mixtures of said isopropylamines; butyl amine, amyl amine, monoisopropanolamine, di-isopropanolamine, triisopropanolamine, and commercial mixtures of said isopropanolamines; ethanolamines such as monoethanolamine, diethanolamine, triethanolamine, and commercial mixtures thereof; polyamines such as aminoethyl ethanolamine, ethylenediamine, diethylenetriamine, hydroxyethyl ethylenediamine, and hexamethylenediamine, hexylamine, cyclohexylamine, dimethylbenzylamine, benzylamine, morpholine, etc. Such salts can be prepared from sodium or potassium salts of the novel sulfosuccinate compounds of our present invention by known metathesis techniques.

The aforesaid unsymmetrical sulfosuccinate diesters are characterized by the fact that there is present in the molecules thereof, connected through one ester linkage to one of the carboxyl groups of maleic anhydride, a free hydroxyl group in the α-position resulting from the utilization of an α-epoxide containing at least 3 carbon atoms in the production of the compounds of our invention, all as is hereafter described in detail and illustrated by the various disclosed embodiments of our invention. The special combination of radicals in the compound of our inventions results in particular properties which effectively adapt various of the compounds to particularly effective utilities in various environments.

In the usual case, the R in formula (I) will be an alkyl derived from a long chain aliphatic monohydric alcohol, or an alkylbenzene derived from an ethoxylated or propoxylated alkyl phenol containing a nuclearly attached alkyl group or groups as described hereinbefore. R' in said formula (I), is an alkyl group which together with the radical:

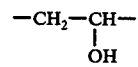

will be derived from an α-epoxide such as propylene oxide or butylene oxide, particular propylene oxide. However, as has been indicated, compounds according to our invention are also obtained where the R of said formula (I) is derived from a $C_1$-$C_3$ aliphatic monohydric alcohol such as methanol, ethanol or propanols, and the:

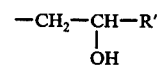

is derived from a $C_8$-$C_{12}$ or $C_8$-$C_{20}$ α-epoxide such as octylene oxide or dodecylene oxide or styrene oxide.

Particularly preferred embodiments of the novel compounds of our invention comprise unsymmetrical sulfosuccinate diesters one carboxyl group of the sulfosuccinate of which is esterified with a $C_8$-$C_{20}$ aliphatic monohydric alcohol, and the other carboxyl group of the sulfosuccinate of which is reacted with propylene oxide to form a propylene glycol ester group.

The aforesaid compounds are useful in various fields where surfactant or wetting-out properties are a desideratum such as, for instance, detergents, emulsifiers, penetrating agents, stabilizing agents, dispersants, emollients, and the like.

Sulfosuccinate surfactants and, more specifically, sulfosuccinate diesters, are known to the art, being disclosed, for instance, in U.S. Pat. Nos. 2,028,091; 2,507,030; 2,887,504; 3,002,994; and 3,481,973. However, so far as we are aware, there has been no prior suggestion or disclosure of any of the compounds of our invention.

In the preparation of the novel compounds of our invention, maleic anhydride is initially reacted with an aliphatic (which term includes cycloaliphatic) monohydric alcohol, or with an ethoxylated or propoxylated alkyl phenol, in proportions such as to produce predominately the maleic acid monoester. Generally speaking, a mole ratio of 1 to about 1.2 moles of maleic anhydride to 1 mole of the aliphatic monohydric alcohol or of the alkyl phenol or of the ethoxylated or propoxylated alkyl phenol results in the production of a reaction product which contains upwards of 90 or 95% of the monoester. It is generally unnecessary to purify the reaction prodduct to separate the monoester but this can be done, if desired, by conventional purification techniques.

In a particularly preferred procedure for the production of the monoester, particularly where the alcoholic reactant with the maleic anhydride is an aliphatic monohydric alcohol, such as, for instance, long chain aliphatic monohydric or fatty alcohols, said alcohols are initially admixed with a small proportion, commonly from about 0.05 to 0.5%, by weight of said alcohol, of an inorganic hydroxide or a basic catalyst, such as sodium hydroxide or potassium hydroxide in strong aqueous solution, and heated to a somewhat elevated temperature, for instance, about 100°–115° C. under vacuum while purging with an inert gas, such as nitrogen, argon, or helium, whereby to remove all or essentially all water from the system, after which the vacuum is released and the alcoholic reactant, at the selected temperature, is admixed with the maleic anhydride and reacted, for instance, at about 70 to about 100° C., until the acid number reaches or approximates that of the desired monoester or half ester. To said monoester is then added the selected α-epoxide to drive the reaction to completion which, in the usual cases, involves the employment of about 0.2 to 0.3 moles excess to effect completion of the reaction in a reasonable length of time. To the resulting unsymmetrical diester there is then added slightly more than 1 mole of the bisulfite per mole of maleic anhydride used and the resulting mixture is heated until the reaction is complete. It should be noted that, in the preparation of the novel compounds of our present invention, whether by the preferred procedure described in this paragraph or otherwise in accordance with our invention, it is essential that maleic anhydride be utilized.

In the preparation of those of the compounds of our invention which are in the form of amine salts, it is sometimes desirable to produce such in substantially anhydrous form, soluble in organic solvents, particularly polar organic solvents such as ethyl alcohol, propyl alcohol, isopropyl alcohol, methyl and ethyl formamides, etc. To this end, for instance, the afore-described diesters can be reacted with a solution containing an organic amine, sufficient water to provide a reaction medium and containing dissolved sulfur dioxide to form a sulfite of said organic amine, and a water-miscible alcohol, for instance, methyl alcohol, ethyl alcohol, n-propanol or isopropyl alcohol, whereby to produce a substantially anhydrous organic amine salt of the said sulfosuccinic acid diesters. For best results, in carrying out such reaction, for each mole of said diester, the solution reacted therewith should contain about 1 mole or slightly more of organic amine or amines, and about 1 mole of water containing about 1 mole of sulfur dioxide.

In the preparation of the novel compounds of our invention by the foregoing method, is important, in order to obtain said compounds, that the sequence of steps noted above be followed, that is, that the maleic acid monoester of the $C_1$–$C_{20}$ aliphatic monohydric alcohol, or of the ethoxylated or propoxylated alkyl phenol, first be provided or prepared after which the reaction with the α-epoxide is carried out, followed by the reaction with the aqueous bisulfite to introduce the sulfonic group into the molecule. Thus, for instance, if the α-epoxide is first reacted with the maleic anhydride and then with (a) the $C_1$–$C_{20}$ aliphatic monohydric alcohol or ethoxylated or propoxylated alkyl phenol, followed by the reaction with the aqueous bisulfite, or (b) the aqueous bisulfite followed by the reaction with the $C_1$–$C_{20}$ aliphatic monohydric alcohol or the ethoxylated or propoxylated alkyl phenol, the products of or contemplated by the present invention are not obtained.

In the reaction of the monoesters with α-epoxides containing at least 3 carbon atoms to produce the intermediate diesters which are then converted into the unsymmetrical sulfosuccinate esters of our invention, said reaction is especially desirably carried out in the presence of a catalyst, particularly a basic inorganic or organic material such as, by way of example, sodium hydroxide, potassium hydroxide, sodium carbonate, potassium carbonate; tertiary amines such as triethylamine and tri-isopropylamine; and quaternary ammonium salts such as tetramethyl ammonium hydroxide, tetraethyl ammonium hydroxide, benzyl trimethyl ammonium hydroxide, and benzyl triethyl ammonium hydroxide. Such catalysts can be used in variable proportions, generally in the range of 0.1 to 2 or 3%, based on the weight of the monoester, depending generally on the basicity of the catalyst.

No novelty is claimed in the monoesters of maleic anhydride with certain of the alcohols as such, namely with $C_1$–$C_{10}$ aliphatic monohydric alcohols, since such compounds and various procedures for their preparation are known to the prior art, and the same is true with respect, per se, to certain of the reaction products of such half esters or monoesters with α-epoxides such as ethylene oxide and propylene oxide.

The R in formula (I) can be derived from straight chain or branch chain aliphatic monohydric alcohols having the formula $R_1OH$ where $R_1O$- is the radical of a $C_1$–$C_{20}$ aliphatic monohydric alcohol, or of an ethoxylated or propoxylated phenol in which there are not more than 3 nuclearly attached alkyl groups, one or two of these containing from 5 to 12 carbon atoms and the third or any second or third, if present, containing $C_1$–$C_3$ carbon atoms, so long as indicated that there is 1, but not more than 2, nuclearly attached radicals containing from 5 to 12 carbon atoms; and in which the number of ethoxy ($-C_2H_4O$) or propoxy ($-C_3H_6O$) groups is from 1 to 6.

The $R_1$ in the formula $R_1OH$, above, can be straight chain or branch chain and, by way of illustration, is derived from such alcohols as methyl alcohol, ethyl alcohol, n-propyl alcohol, isopropyl alcohol, n-butyl alcohol, isobutyl alcohol, cyclohexanol, n-amyl alcohol, isoamyl alcohol, n-hexyl alcohol, isohexyl alcohol, 2-ethyl hexyl alcohol, 2-ethyl octyl alcohol, n-nonyl alcohol, isononyl alcohol, n-decyl alcohol, isodecyl alcohol, undecyl alcohol, n-dodecyl alcohol, isododecyl alcohol, tridecyl alcohol, tetradecyl alcohol, pentadecyl alcohol, hexadecyl alcohol, heptadecyl alcohol, and octadecyl alcohol, and mixtures thereof as in commercial mixtures of fatty and other alcohols; oxo alcohols such as the primary monohydric saturated aliphatic $C_{10}$–$C_{20}$ alcohols as, for instance, oxo tridecyl alcohol and oxo hexadecyl alcohol (see U.S. Pat. No. 2,965,678), and they can be derived from grain sources, fatty triglycerides, and petroleum sources including kerosene fractions and polymerized olefins such as polypropylenes, for instance, propylene trimers and tetramers, from oxo alcohol procedures, and by Ziegler catalytic and other chemical procedures. Also included in such aliphatic monohydric alcohols are those derived by adducting 1 mole of such alcohols as octyl, decyl, and dodecyl alcohols, or analogous branched chain alcohols, with 1 to 4 moles of ethylene oxide, or by adducting 1 mole of such alcohols as hexyl, octyl, decyl, or dodecyl alcohols, or analogous branched chain alcohols, with from 1 to 4 moles of propylene oxide.

Where in formula (I) the compounds comprise those which include a radical of an ethoxylated or propoxylated alkyl phenol in which there are not more than 3 alkyl groups as described hereinabove, said alkyl phenols can conveniently be represented by the formula:

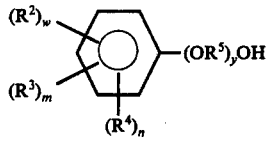
(II)

where $R^2$ and $R^3$ are the same or dissimilar $C_5$-$C_{12}$ alkyl radicals, $R^4$ is a $C_1$-$C_3$ alkyl radical, $R^5$ is $C_2H_4$ or $C_3H_6$; each of $w$, $m$, and $n$ is zero to 1, subject to the proviso that, when $w$ is zero, $m$ is 1 or 2, and $y$ is 1 to 6.

Illustrative examples of such ethoxylated and propoxylated alkyl phenols from which compounds of our invention can be prepared are the adduct of 1 mole of octyl phenol with 2 moles of ethylene oxide; the adduct of 1 mole of nonyl phenol with 3 moles of ethylene oxide; the adduct of 1 mole of nonyl phenol with 1 mole of propylene oxide; the adduct of 1 mole of diamyl phenol with 3 moles of ethylene oxide; the adduct of 1 mole of dodecyl phenol with 2 moles of ethylene oxide the adduct of 1 mole of dioctyl phenol with 2 moles of propylene oxide; the adduct of 1 mole of dinonyl phenol with 3 moles of ethylene oxide; the adduct of 1 mole of nonyl hydroxy toluene with 2 moles of ethylene oxide the adduct of 1 mole of isopropyl nonyl phenol with 2 moles of ethylene oxide; and the adduct of 1 mole of dinonyl isopropyl phenol with 3 moles of ethylene oxide.

The α-epoxides which are utilized in the preparation of the novel compounds of the present invention and from which the radical:

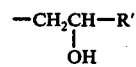

of formula (I) is derived include, by way of illustrative examples, propylene oxide, butylene, pentylene, hexylene, heptylene, octylene, nonylene, decylene, dodecylene, tetradecylene, pentadecylene, hexadecylene, and octadecylene oxides, as well as styrene oxide and similar α-epoxides derived from analogous alkenyl benzenes.

Illustrative examples of chemical compounds falling within the scope of our invention are the following:

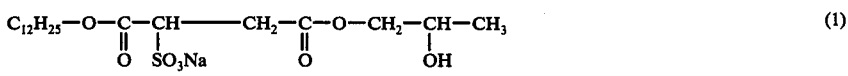 (1)

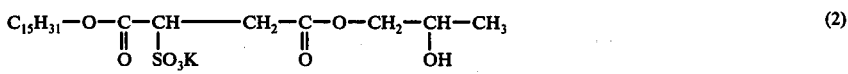 (2)

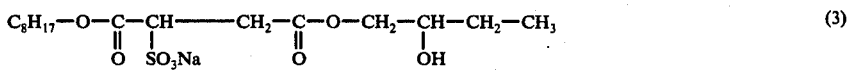 (3)

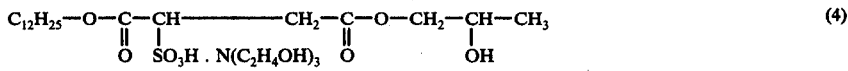 (4)

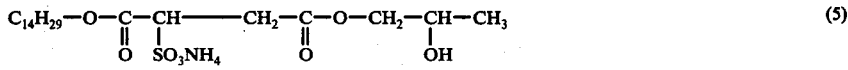 (5)

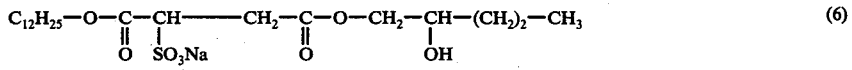 (6)

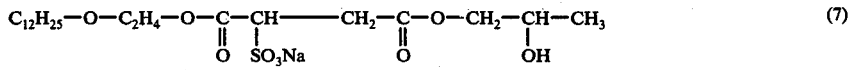 (7)

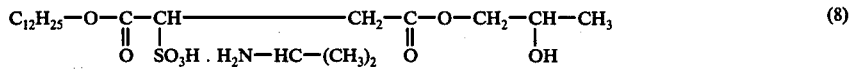 (8)

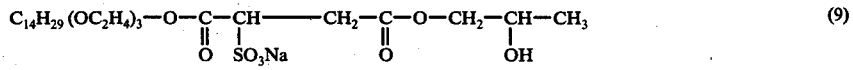 (9)

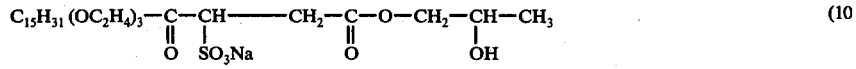 (10)

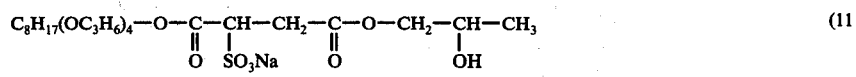 (11)

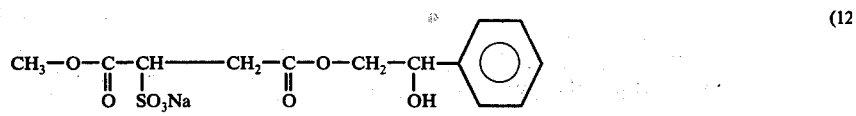 (12)

-continued

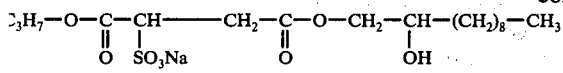  (13)

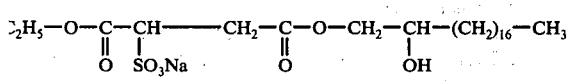  (14)

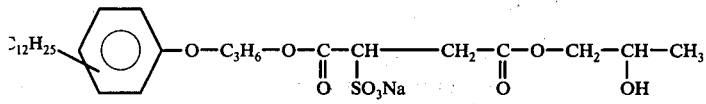  (15)

(16)

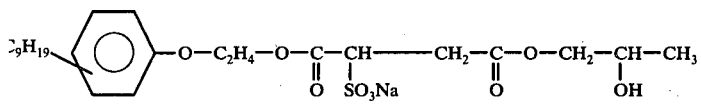

(17)

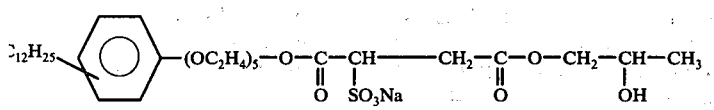

(18)

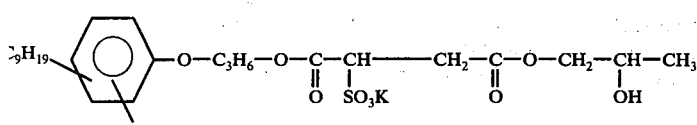

The following examples are illustrative of the preparation of typical compounds of the present invention. All temperatures recited are in degrees Centigrade.

EXAMPLE I (a) To 1242g (6.06 moles) of "NEODOL 25" (a commercial product consisting mainly of a mixture $C_{12}$–$C_{15}$ aliphatic monohydric alcohols having an average molecular weight of about 205) are added 1.4g of KOH in 1ml of water, and the mixture is heated to about 105° under a vacuum 25mm. of Hg while purging with gaseous nitrogen, and then held at such temperature for about ½ hour. It is then cooled to about 75°, the vacuum is released, and to it is added 600g (6.12 moles) of maleic anhydride, and the reaction mixture is maintained at about 75° for approximately 2 hours at the end of which time the acid value is 3.47 meq/g, indicating formation of the maleic acid monoester of said mixture of alcohols.

(b) The monoester produced in part (a) hereof is placed in an autoclave heated to 100° and to it is added 456g (7.85 moles) of propylene oxide over a period of 5 hours, at the end of which time the acid value is 0.001 meq/g. The resulting diester contains, in the molecule, approximately 1.2–1.3 oxypropylene or propoxy groups.

(c) To the diester produced in part (b) hereof there is added 600 ml of water and 1530g of 42% aqueous sodium bisulfite solution (6.18 moles) and heated to 90°. An almost immediate exothermic reaction occurs and the pressure in the autoclave rises to of the order of 5 to 10 pounds per square inch. The reaction is complete in about ½ hour. A somewhat viscous, light yellow solution is obtained containing approximately 0.5% free sodium sulfite and 67% solids. On the basis of the solids content, the sulfosuccinate surfactant produced shows the following properties:

| Weight % In Water Solution | Draves Wetting Test Sink Time-Seconds |
| --- | --- |
| 0.067 | 40 |
| 0.168 | 17 |
| 0.335 | 12 |

The surface tension of a 0.05% water solution is 32.1 dynes/cm.$^2$

EXAMPLE II

To 500g (3.7 moles) of "ALFOL 610" ($C_6$–$C_{10}$ synthetic alcohol, mean molecular weight 136) is added 1.0g of NaOH dissolved in 2ml of water, and this mixture is heated to 85° in vacuo for ½ hour. To it is then added 361g (3.7 moles) of maleic anhydride at 70° and the resulting reaction mixture is maintained at this temperature for 1 hour. At the end of this period, the acid value is 4.25 meq/g. The resulting monoester is placed in a stirred autoclave heated to 100° and to it is added 285g (4.9 moles) of propylene oxide over a period of 2 hours at 30 psi pressure, then stirred an additional 3 hours at this temperature. At this point the pressure in the autoclave is about 10 pounds per square inch. The acid value of the diester, which contains, in the molecule, approximately 1.3 propoxy groups, is 0.01 meq/g. The said diester is stripped in vacuo at 95°–100° and to it at this temperature is added 970g of a 40% aqueous sodium bisulfite solution (3.7 moles) over a period of 1 hour, and to this solution is then added 345ml of 95° water. The final sulfosuccinate product is a mobile liquid at room temperature which is completely soluble in water.

EXAMPLE III

To 316g (2.02 moles) of the isopropyl alcohol monoester of maleic anhydride is added 0.5g of sodium methylate and 300g (2.17 moles) of a technical grade 1,2-octene oxide (M.W. 136) having an epoxide content of 7.25 meq/g. The reaction mixture is heated to 100° for 10 hours, at the end of which period the acid value is 0.05 meq/g. The resulting diester is stripped at 100° and 0.1 mm pressure, and to it is added 550g of a 42% aqueous sodium bisulfite solution (2.22 moles) at 100°. After 1 hour, the reaction is complete and an additional 500 parts of 95° water is added. The final sulfosuccinate product is a clear, slightly amber solution, which is completely miscible with water.

EXAMPLE IV

To 400ml of water are added 34g of the sulfosuccinate surfactant prepared in Example II, 1.25g of potassium persulfate, 7g of hydroxyethyl cellulose ("Cellosize WP-09", Union Carbide Corporation), and 1.3g of sodium bicarbonate. This solution is heated to 70° and to it is added 70°–75°, in separate streams, over a period of 4 hours, 550g of vinyl acetate and a solution of 1.25g of sodium persulfate in 50ml of water. When the addition is complete, the temperature is raised to 90° for ½ hour. The resulting vinyl acetate latex contains 55% solids and shows no separation after standing for 6 months.

EXAMPLE V

The sulfosuccinate surfactant product of Example III is used in an emulsion polymerization process as described in Example IV with similar results.

EXAMPLE VI the procedure described in Example I is carried out except that, in part (a), in place of the 1242g of "NEODOL 25", there is used 1664g (6.06 moles) of an adduct of 1 mole of nonyl phenol with 1.2 moles of ethylene oxide. The balance of Example I is carried out using the same amounts of the specified ingredients. The sulfosuccinate product obtained corresponds essentially to the formula:

$$C_9H_{19}-C_6H_4-O-C_2H_4-O-\underset{\underset{O}{\|}}{C}-\underset{\underset{SO_3Na}{|}}{CH}-CH_2-\underset{\underset{O}{\|}}{C}-O-CH_2-\underset{\underset{OH}{|}}{CH}-CH_3$$

EXAMPLE VII

The procedure described in Example II is carried out except that, in place of the 500g of "ALFOL 610", there is used 1133g (3.7 moles) of an adduct of 1 mole of nonyl phenol with 2 moles of ethylene oxide. The sulfosuccinate product obtained corresponds to the formula:

$$C_9H_{19}-C_6H_4-O-C_2H_4-O-C_2H_4-O-\underset{\underset{O}{\|}}{C}-\underset{\underset{SO_3Na}{|}}{CH}-CH_2-\underset{\underset{O}{\|}}{C}-O-CH_2-\underset{\underset{OH}{|}}{CH}-CH_3$$

EXAMPLE VIII

The procedure described in Example II is carried out except that, in place of the 500g of "ALFOL 610", there is used 482g (3.7 moles) of 2-ethyl hexanol. The sulfosuccinate product obtained, containing 69.6% solids, has a critical micelle concentration of 1.2% which renders it especially desirable for use in emulsion polymerization procedures such as are shown in Example IV above.

We claim:

1. An unsymmetrical sulfosuccinate surfactant having the formula:

$$R-(OR'')_x-O-\underset{\underset{O}{\|}}{C}-\underset{\underset{SO_3M}{|}}{CH}-CH_2-\underset{\underset{O}{\|}}{C}-O-CH_2CH-R'$$
$$\phantom{xxxxxxxxxxxxxxxxxxxxxxxxxxxxxxxxx}\underset{OH}{|}$$

where:
  R = $C_1$-$C_{20}$ alkyl, or an alkylbenzene radical having at least 1, but not more than 3, nuclearly attached alkyl groups and at least 1, but not more than 2, of these alkyl groups containing 5 to 12 carbon atoms and the said such other alkyl group or groups, as may be present, containing 1 to 3 carbon atoms,
  R' = alkyl containing 1 to 18 carbon atoms or a benzene radical,
  R'' = ethylene or propylene,
  x = 0 to 6 and is at least 1 when R = an alkylbenzene radical,
with the proviso that the sum of the number of carbon atoms in R and R' is from 5 to 33 and that there is a difference in the number of carbon atoms in R and R' which difference is at least 4; and M is a cation selected from the group of alkali metals, ammonium, alkaline earth metals and water soluble organic amines.

2. A surfactant according to claim 1, in which the difference in the number of carbon atoms between R and R' is from 6 to 16.

3. A surfactant according to claim 1, in which R is alkyl containing from 8 to 15 carbon atoms and R' is methyl.

4. A surfactant according to claim 3, in which R is a straight chain alkyl.

5. A surfactant according to claim 1, in which R contains from 3 to 18 carbon atoms and is a branched chain alkyl.

6. A surfactant according to claim 1, in which R-(OR'')$_x$— is:

$$\underset{(R^3)_m}{\overset{(R^2)_w}{\phantom{X}}}C_6H_2\underset{(R^4)_n}{\overset{(OR^5)_y-}{\phantom{X}}}$$

where $R^2$ and $R^3$ are the same or dissimilar $C_5$-$C_{12}$ alkyl radicals, $R^4$ is a $C_1$-$C_3$ alkyl radical, $R^5$ is $C_2H_4$ or $C_3H_6$, each of w, m, and n is zero to 1, subject to the proviso that, when w is zero, m is 1 or 2, and y is 1 to 6.

7. A surfactant according to claim 1, in which R-(OR'')$_x$— is:

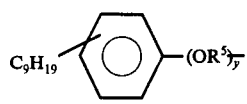
where $R^5$ is $C_2H_4$, and y is 1 to 6.
8. A surfactant according to claim 1, in which R is a $C_1$-$C_3$ alkyl radical, and R' is an alkyl radical containing from 6 to 10 carbon atoms.
* * * * *